United States Patent

Böhm

[11] Patent Number: 5,320,733
[45] Date of Patent: Jun. 14, 1994

[54] SENSOR SYSTEM

[75] Inventor: Alfred Böhm, Viechtach, Fed. Rep. of Germany

[73] Assignee: Ultrakust electronic GmbH, Gotteszell, Fed. Rep. of Germany

[21] Appl. No.: 717,832

[22] Filed: Jun. 21, 1991

[30] Foreign Application Priority Data

Dec. 21, 1990 [EP] European Pat. Off. ........ 90125103.3

[51] Int. Cl.$^5$ .............................................. G01N 27/407
[52] U.S. Cl. .............................. 204/408; 204/153.17; 204/153.18; 204/409; 204/415; 204/424
[58] Field of Search .................. 204/153.22, 153.17, 204/153.18, 415, 421–429, 409, 408

[56] References Cited

U.S. PATENT DOCUMENTS

| Re. 31,914 | 6/1985 | Oswin et al. | 204/432 |
| 3,413,199 | 11/1968 | Morrow | 204/153.13 |
| 3,442,773 | 5/1969 | Wilson | 204/427 |
| 3,546,086 | 12/1970 | Sayles | 204/427 |
| 4,384,925 | 5/1983 | Stetter et al. | 204/406 |
| 4,394,222 | 7/1983 | Rohr | 204/427 |
| 4,571,285 | 2/1986 | Nakazawa et al. | 204/425 |
| 4,828,673 | 5/1989 | Maeda | 204/424 |
| 4,900,405 | 2/1990 | Otagawa et al. | 204/280 |
| 5,145,566 | 9/1992 | Logothetis et al. | 204/429 |

Primary Examiner—T. Tung
Attorney, Agent, or Firm—Keck, Mahin & Cate

[57] ABSTRACT

The invention relates to a sensor system for determining the moisture content in a gas to be measured. On the basis of two current saturation ranges during the determination of the moisture content with the aid of a zirconia sensor, according to the invention two spatially separated sensors are provided, which are operated at different voltages corresponding to the individual saturation current ranges. By further evaluation of the signals, this permits a very precise, on-line determination of the moisture content of the gas to be measured.

9 Claims, 5 Drawing Sheets

SENSOR SYSTEM

BACKGROUND OF THE INVENTION

The invention relates to a sensor system located in a measurement casing according to the preamble of claim 1.

A comparable sensor system is e.g. known from EP 0 166 530 B1 or DE 37 02 838 A1.

The principle of these known sensor systems makes it possible to measure the oxygen partial pressure in a gas or in a gaseous mixture and in addition the moisture content of the gas can be determined.

These sensor systems have an oxygen-conducting plate for the individual sensor and which is in particular made from zirconia ($ZrO_2$). When a voltage is applied to the electrodes on said plate the oxygen is pumped out of the interior of the diffusion casing. This pumping effect resulting from the applied voltage is greater than the quantity of the oxygen entering through the gas diffusion opening of the sensor. The current flowing through the zirconia plate is therefore dependent on the rate of the oxygen ions diffusing through the zirconia plate. However, as the oxygen flow quantity is limited due to the gas diffusion opening, there is initially a current saturation at a given voltage and in this phase the number of oxygen ions diffusing through the zirconia plate corresponds to the oxygen quantity entering through the gas diffusion opening.

When the aim is to establish the moisture content of a corresponding gas or air using such a sensor system, it must be borne in mind that primarily the oxygen partial pressure is reduced by the water content of the gas to be measured. Therefore the current saturation range is formed at a lower current intensity.

On further increasing the voltage between the electrodes on the zirconia plate, due to the diffusion of oxygen through the gas diffusion opening the current flow initially remains constant until, as a result of the higher voltage, the water vapour or steam decomposes into oxygen and hydrogen. This oxygen resulting from the dissociation of the steam now brings about an increase of the current flow. Thus, a further current saturation range forms, which in absolute values is above the current flow of the same gas without moisture.

Thus, for calculating the moisture content of a moist, oxygen-containing gas two saturation current ranges are obtained, whose current difference makes it possible to determine the moisture content in the gas to be measured.

In known sensor systems operating with the two aforementioned different current levels, an important disadvantage occurs in that on modulating the zirconia sensor to the two different voltage or current levels overshoots occur, so that no details on the corresponding moisture content can be obtained until there is a stable build-up.

It has also been found that the determination of an optimum modulation function is relatively difficult in the case of different moisture contents and consequently the known sensor systems suffer from a considerable time loss when calculating the moisture content.

SUMMARY OF THE INVENTION

The object of the invention is consequently to overcome the afore-mentioned disadvantageous effects and to provide a precisely and rapidly operating sensor system.

This object is achieved by the features of the characterizing part of claim 1.

A fundamental idea of the invention is consequently that the sensor system is provided with two spatially separated sensors having the same construction, particularly in the form of zirconia sensors. One sensor is operated at a current or voltage level causing the dissociation of the water vapour or steam contained in the gas to be measured. The other sensor, which is spaced therefrom, is operated at the lower current or voltage level, which is clearly below the dissociation level and where correspondingly there is no need to take account of the oxygen partial pressure resulting from the steam. The output signals of the two sensors determined in this way can consequently be simultaneously processed in parallel in a microprocessor and enable information to be directly obtained in real time concerning the moisture content of the gas to be measured.

In order to avoid a falsification of the measured results of the two sensors, appropriately two separate gas flows are formed, which are supplied to the individual sensors. It is advantageous to use an internal casing within the actual measurement casing and which contains the two sensors and which either has a channel means to the two sensors or is separated by a wall into two channel regions.

In another simplified embodiment the two sensors are successively arranged in the gas flow introduced into the inner casing. The first sensor so to speak functions as a "dry" sensor, whereas the second sensor behind it in the gas flow can be looked upon as a "dissociation" sensor. Also in the case of this sensor system design precise information is obtained on the moisture content in the gas to be measured without the known disadvantages.

Independently of the specific construction of the sensor systems, it is ensured that both sensors are located in a gas or gas flow at the same temperature, which is achieved by the heating device provided and the temperature sensor with a corresponding control.

The oxygen pumping action of the zirconia plate of the sensors is most marked at a temperature of approximately 450° C. Thus, with the sensor system is connected a heating device, which maintains the sensors at this temperature. This also avoids major changes to the oxygen diffusion characteristics through the zirconia plates caused by the temperature.

However, the diffusion behaviour can be influenced by a different temperature of the gas to be measured. Thus, upstream of the gas diffusion opening is positioned a temperature measuring and regulating device, which heats or cools the gas to a specific and clearly defined temperature and consequently compensates temperature fluctuations of the gas to be measured or allows the measurement of gases in a large temperature range. This is very advantageous, because the sensor does not have to be recalibrated for each measurement gas temperature.

According to a further development the sensor system is placed in a measurement casing, which has in its interior a heating device. The gas to be measured flows constantly through this measurement casing, so that in the latter there is no formation of a "microclimate", i.e. so that in the measurement casing the moisture content of the gas to be measured does not change due to lack of convection on heating. Thus, certain walls of the measurement casing are at least made gas-permeable. Through the arrangement of the measurement casing in the measurement gas or by a suction mechanism for the same, it is ensured that through the measurement casing there is a forced convection of the gas to be measured.

The temperature sensor for the temperature measuring and regulating device is advantageously positioned between the heating device and the sensor, so that it is possible to accurately set the temperature of the gas to be measured at the entrance to the gas diffusion opening.

In order to prevent the formation of zones of different temperature in the measurement casing, the heating elements of the heating device are positioned close to the inner walls of the measurement casing and surround an inner casing, in which the sensors are at least largely located.

As a result of such a measurement casing the temperature of the gas to be measured is increased to the planned value and as a result of the forced convection through the measurement casing no change to the moisture content of the gas to be measured in the measurement casing is possible.

The gas-permeable measurement casing walls can be constituted by a PTFE-sheet, so that said walls simultaneously serve as filters and prevent contamination of the sensors and in particular the gas diffusion opening thereof.

As a result of the switching on and off of the sensor system the measurement casing can be disconnected from a supply of the gas to be measured and connected to a dry gas supply, so as to prevent the formation of residual moisture in the diffusion casing. On heating the sensors this residual moisture can lead to the destruction thereof. In addition, on cooling the sensor system, the moisture of the gas to be measured can condensate out in the diffusion casing unless switching to a dry gas supply takes place prior to cooling. The heating mechanism for the sensor system is consequently provided with a control, which controls the switching of the gas supply and the control of the cooling or heating speeds for the sensors.

The electrodes of the sensors are connected to a function generator, which keeps the two sensors at different voltage levels. The voltage values are in the current saturation ranges corresponding to the oxygen partial pressure with and without additional moisture hydrolysis.

For calculating the steam partial pressure the function generator is advantageously connected to electronics, which compares the values of the current flow of the sensors with the stored current-moisture content characteristics and calculates from these the steam pressure of the gas to be measured.

As a result of the invention it is not necessary to calibrate the sensor system to a specific measurement gas temperature and instead the latter is adapted to the set sensor system temperature.

Thus, e.g. the temperature can be calibrated to 120° C. and the measured gas can be set to the sensor system calibration temperature of 120° C. by means of a suitable filter and cooling/heating device. The measured gas temperature is determined by means of a temperature sensor, which is once again used for controlling the temperature. The measured gas temperature is chosen so high that it is possible to avoid a condensing out of steam or other substances (e.g. oils) contained in the measurement gas.

Sensors up to a use temperature of 150° C. contain an incorporated PTFE-sheet filter, which allows the passage of steam, but holds back condensation droplets, which could destroy the sensors. Therefore it is possible to use the sensor up to the range close to the dew point.

The gas used for the moisture measurement can be recycled in the case of environmentally prejudicial processes, because the sucked in quantity of the gas to be measured is very small. Suction takes place through an ejector or a suitable pump. As a function of the measurement conditions the gas exchange occurring due to natural convection or diffusion may be adequate. It is optionally possible to have a flow of the gas to be measured through the sensor system by convection only. However, the setting of a clearly defined flowrate by means of a suction device has the advantage that the measurement gas flowrate is kept constant, which may have a certain influence on the measurement result. Measurement errors are consequently minimized and the measurement gas flowrate is limited in order to prevent marked cooling of the measuring apparatus or the measurement gas.

On obtaining the stream partial pressure of a measurement gas, it is also possible to calculate back the oxygen partial pressure in the measurement gas, if the measurement characteristics of the sensors are available and can be obtained by calibration measurements.

Advantageous further developments of the invention form the subject matter of subclaims.

BRIEF DESCRIPTION OF THE DRAWINGS

The invention is described in exemplified manner hereinafter relative to the following drawings, wherein show.

DESCRIPTION OF THE PREFERRED EMBODIMENT

Figure 1:
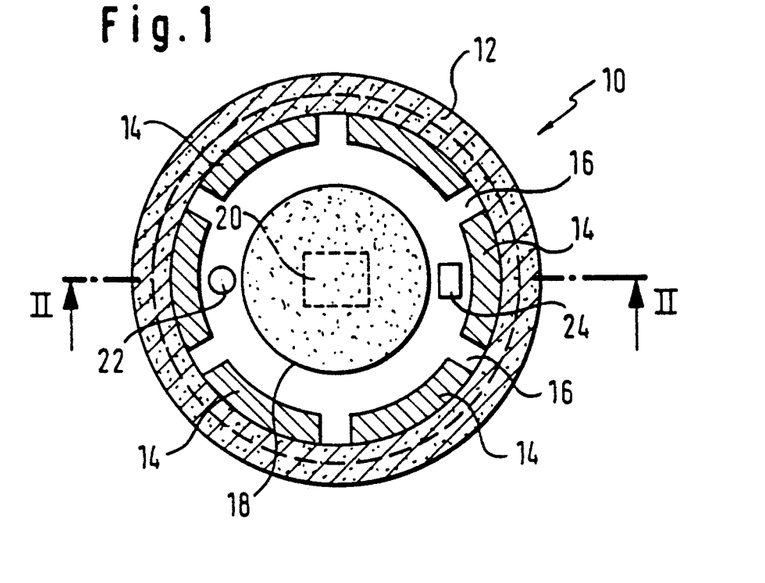
FIG. 1 A cross-section through a first sensor system.

FIG. 1 shows a sensor system for determining the steam partial pressure of a gas or gaseous mixture to be measured.

The sensor system 10 has a cup-shaped, cylindrical measurement casing 12, whose walls are gas-permeable and constructed as filters. In the vicinity of the inner walls of the measurement casing 12 are positioned the heating elements 14 of a heating device. The heating elements 14 surround in circular manner the interior of the measurement casing 12 and have openings 16 passing in the direction of the cylinder axis of the measurement casing 12 in order to permit a radial passage of the gas to be measured. In the interior of the measurement casing 12 is provided a hemispherical PTFE-sheet filter 18 concentrically positioned with respect to the walls of the casing 12 and the heating element 14 and which is only permeable for gases and water vapour or steam. An oxygen sensor 20, a temperature sensor 22 and a flow detector 24 are located within the filter.

The temperature sensor 22 is directly coupled to the heating device and as a result a clearly defined, constant temperature always prevails within the measurement casing 12. the flow detector 24 records the gas flow within the measurement casing 12 and gives a fault or error signal if there is no gas flow. This prevents the formation of a microclimate, when the steam pressure of the gas below the casing 12 could be set at a different value from that in the overall volume of the gas to be measured. The sensor 20 is kept at a constant temperature of approximately 450° C.

Figure 2:
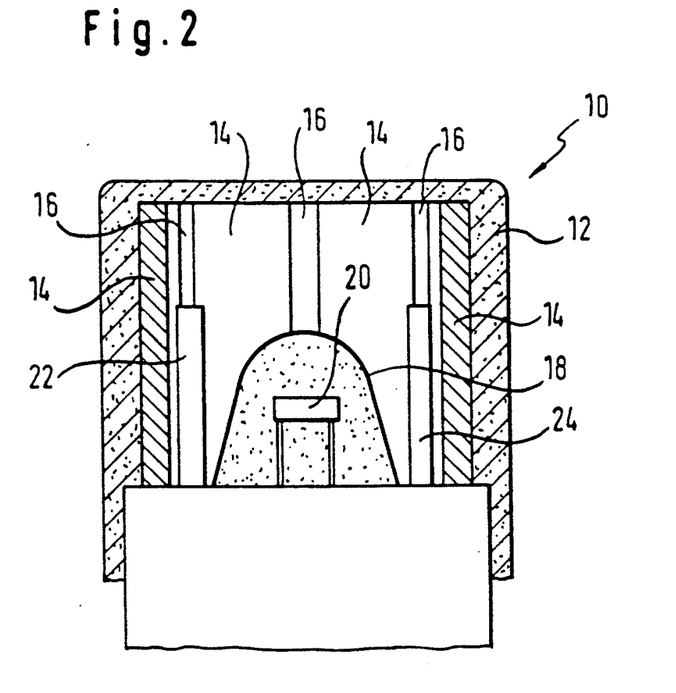
FIG. 2 A section II—II according to FIG. 1.

Through the sensor arrangement shown in FIGS. 1 and 2 without changing the steam pressure of the gas, it is heated to a clearly defined temperature and supplied to the sensor 20. Obviously the heating device can be replaced by an air conditioner, the heating element 14 then being constructed as heating or cooling elements. Such an apparatus would allow the moisture measurement of a gas having a temperature higher than the desired measurement gas temperature.

The PTFE filter keeps vapours of organic compounds away from the sensor 20, because they could lead to a blockage of the gas diffusion opening in the sensor. Other filters are used for higher temperatures.

By means of the heating device with the heating elements 14, the gas to be measured can be heated e.g. to a temperature of 120° to 300° C. (as a function of the sensor setting), which allows the measurement of a gas with a random temperature below this without having to carry out additional calibrations.

Figure 3:
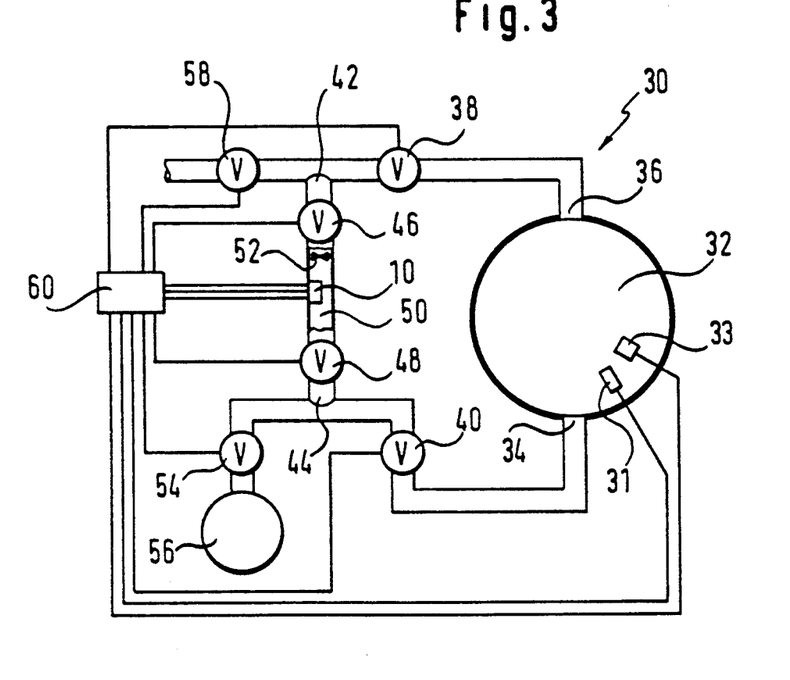
FIG. 3 An apparatus for measuring the moisture content of a gaseous mixture with incorporated sensor system.

FIG. 3 shows the sensor system 10 installed in a measuring apparatus 30 for measuring the moisture content of a measurement gas. The latter is located in a reaction vessel 32, which has an outlet line 36 and an inlet line 34 to the apparatus 30. By means of controllable valves 38, 40 the outlet line 36 and the inlet line 34 are in each case connected to a T-coupling 42, 44, whose vertical legs are connected by controllable valves 46, 48 to a measuring tube 50. The latter contains the sensor system 10 and a circulating fan 52. By means of a further controllable valve 54 a dry gas source 56 is connected to the T-coupling 44 connected to the inlet line 34. The T-coupling 42 connected to the outlet line 36 is connected by means of a controllable valve 58 to an exhaust or disposal mechanism. The sensor system 10 is connected to a control unit 60, which regulates the operation of the moisture sensor 20 and controls the position of the controllable valves 38, 40, 46, 48, 54, 58. The reaction vessel 32 contains an additional temperature sensor 33 and a pressure sensor 31, in order to establish the actual temperature and pressure of the measurement gas outside the measuring apparatus, so as to be able to derive therefrom correction values for the gas moisture content, as well as other characteristic quantities (dew point).

The operation of the measuring apparatus 30 will now be described.

On switching on the measuring apparatus the valves 38, 40 between the T-coupling 42, 44 and the reaction vessel 32 are closed. The remaining valves 46, 48, 54, 58 are opened and the fan 52 is put into operation, so that a dry gas is supplied to the sensor system 10. This prevents moisture from penetrating the sensor 20 and therefore the destruction of the sensor during the following heating phase. If the sensor system 10 was cooled in dry gas in a preceding measurement cycle, only the valves 46 and 48 at the longitudinal ends of the measuring tube 50 would have to remain closed until the operating temperature of the sensor 20 is reached. The valves 54 and 58 are now closed and the valves 46, 48, 38, 40 are opened for connecting the measuring tube 50 to the reaction vessel 32. As a result of the suction action of the fan 52 a gas flow is obtained in the measuring tube 50. The temperature sensor 22 in the sensor system 10 measures the temperature of the throughflowing measurement gas and passes the measurement signal to the control unit 60, which by means of a heating device with the elements 14, regulates the measurement gas temperature to a desired value. This enables the moisture measurement to be staggered in the manner to be described hereinafter until the measurement is ended.

In this case the valves 38, 40 for connecting the T-coupling 42, 44 to the reaction vessel 32 are closed and the measuring tube 50 is again connected to the dry gas supply 56. The measuring tube 50 is flooded with dry gas until the residual moisture content is approximately 0. Valves 46 and 48 are then closed and the heating mechanism for the sensor is switched off. The decrease of the moisture content can be measured by means of the sensor 20. By cooling in the dry gas condensation of the moisture on the inner walls of the sensor diffusion casing is prevented, which would have led to a bursting or forcing open of the sensor during the following heating process.

Figure 4:
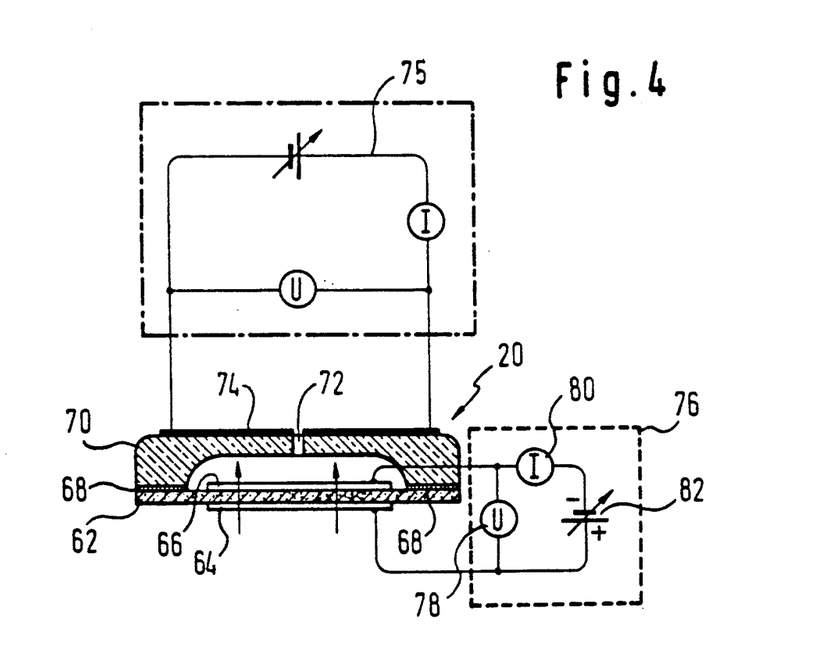
FIG. 4 A sensor for determining the steam partial pressure.

FIG. 4 shows a sensor 20 as used in a sensor system 10. The sensor 20 comprises a stabilized zirconia plate 62, which permits an oxygen diffusion and which is provided with flat electrodes 64, 66 on its opposite surfaces. On one side of the zirconia plate 62 a cup-shaped diffusion casing 70, which is preferably made from glass, is connected in gas-tight manner by means of a glass frit 68. On its top surface, the diffusion casing 70 has a central gas diffusion opening 72. A filament winding 74 is evaporation coated on to the outside of the diffusion casing 70. Circuit 75 controls filament winding 74. The flat electrodes 64, 66 are preferably porous platinum electrodes, which allow the passage of oxygen ions through the zirconia plate 62.

The electrodes 64, 66 are connected to a function generator 76, which forms a component of the control unit 60 of FIG. 3. The function generator 76 has a voltmeter 78 for determining the voltage at the electrodes 64, 66 and an ammeter 80 for determining the current flowing between the electrodes 64, 66. The function generator 76 can also have a controllable voltage source 82 enabling an electric field to be produced in the zirconia plate 62, so that oxygen ions are diffused to the outside from the diffusion casing 70.

The gas diffusion opening 72 of the diffusion casing 70 is dimensioned in such a way that on applying a suitable electric field between the electrodes 64, 66, the diffusion of the oxygen ions through the zirconia plate 62 is greater than the corresponding diffusion of oxygen through the gas diffusion opening 72 into the diffusion casing 70. Thus, the gas diffusion through the gas diffusion opening 72 is the step determining the speed which, on measuring a dry measurement gas, leads to the formation of a current saturation range 84 in the current-voltage characteristic of the sensor (FIG. 5).

The gas diffusion opening 72 has a diameter of a few $O_2$ molecules. The diffusion casing can also have a porous construction and consequently permits the rediffusion of $O_2$. In this case a large number of non-shape defined gas diffusion openings would be formed in the diffusion casing.

Figure 5:
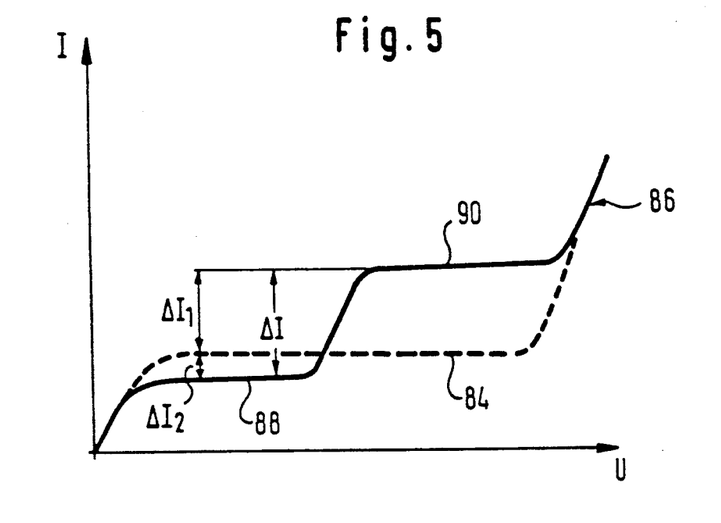
FIG. 5 A voltage-current diagram obtained with the sensor of FIG. 4 for determining the steam partial pressure from the characteristic quantities obtained.

If an oxygen partial pressure is now added to the same gas, then the current-voltage characteristic 86 shown in FIG. 5 is obtained. In said characteristic 86 is formed a first saturation current range 88 in which the current flow is constant over a larger voltage range. The level of the current flow in this range 88 is below that of the dry gas, because the oxygen partial pressure is lower due to the additionally present steam partial pressure. On further increasing the voltage then a second saturation current range 90 is obtained, which results from the fact that the steam entering through the gas diffusion opening 72 is decomposed into hydrogen and oxygen, the latter contributing to the current flow in addition to the oxygen partial pressure of the measurement gas which is in any case present. The difference $\Delta I$ between the current flow of the two saturation current ranges 88 and 90 is a measure of the steam pressure in the measurement gas.

It is also possible to use the steam partial pressure through the spacing, i.e. the current difference $\Delta I_1$ between the current saturation range 90, the current saturation range 84 of the dry measurement gas and/or the current difference $\Delta I_2$ between the current saturation range 84 of the dry measurement gas and the current saturation range 88.

In known manner, the zirconia plate 62 is stabilized with yttrium or calcium.

The forced convection through the measurement casing can be achieved through a corresponding arrangement of the heating elements. It is possible to utilize the chimney effect of the measuring apparatus during the heating of the measurement gas.

A change to the rise and fall time of the voltage supplied to the electrodes 64, 66 could take place in the form of a triangular sine or rectangular characteristic. In addition to the heating means 14, it is also possible to regulate the platinum heating electrode 74, in that its internal resistance is measured and this is maintained constant by means of a suitable regulating device.

On the abscissa in FIG. 5 is plotted the voltage U applied to the electrodes 64, 66 and measured with the voltmeter 78 in FIG. 4, whilst on the ordinate is plotted the current I measured with the ammeter 80.

Whilst taking account of FIG. 5, according to which two saturation current ranges 88 and 90 for the oxygen partial pressure without dissociation of hydrogen molecules and with dissociation are known, the sensor system 10 or 100 is operated with two spatially separated sensors 20. For better differentiation, the sensor 20 is subsequently separated into the two sensors 91 and 92.

Figure 6:
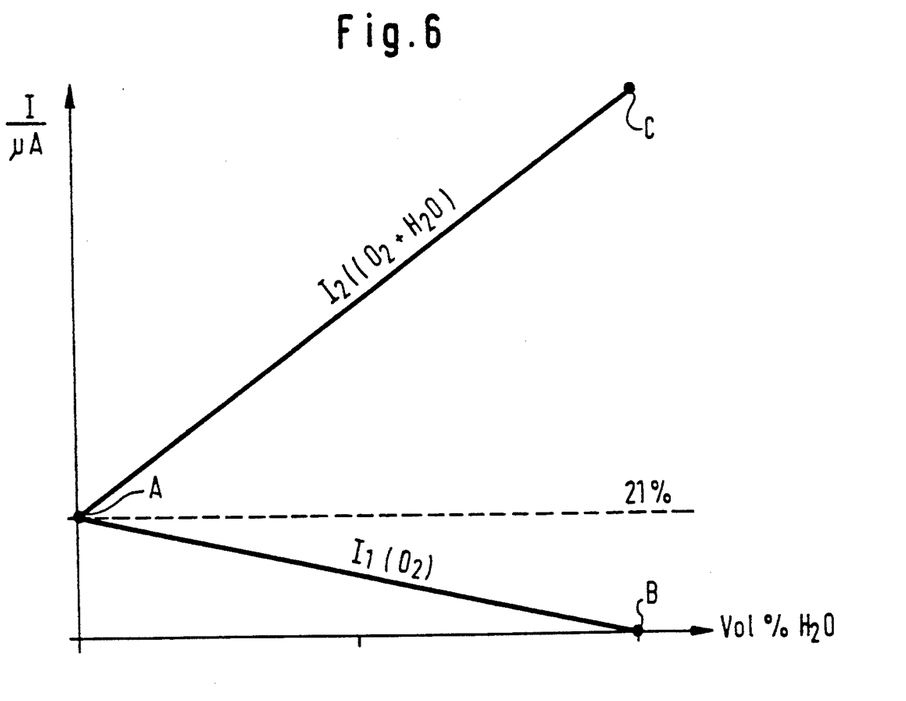
FIG. 6 A diagrammatic representation of the current-moisture diagram of the two sensors used in the sensor system.

FIG. 6 diagrammatically shows the current characteristic of the sensor 91 as $I_1$ as a function of the oxygen content of the gas or air (vol % $H_2O$). The current path $I_2$ of the second sensor 92 is shown as the upper straight line.

Point A marks the state of the dry air with approximately 21% oxygen, so that in this range it is possible to speak of an almost pure oxygen line with respect to the sensors 91 and 92. Point B indicates the oxygen content in the case of steam-saturated air, based on the sensor 91, whose current path $I_1$ reproduces the oxygen content without steam dissociation. With increasing moisture content or increasing steam content in the gas to be measured, there is consequently a roughly linear fall of the current $I_1$ from an initial value at A to 0.

The current characteristic $I_2$ for the second sensor 92 has a straight, opposite path. As this sensor 92 is operated roughly at a voltage of 1.8 V and consequently a dissociation of the steam in the gas is possible, this second current path $I_2$ represents the oxygen atoms resulting from the dissociation of the steam.

The measured current values $I_1$ and $I_2$ or their difference consequently makes it possible to precisely determine the moisture content present in the gas to be measured in an on-line, real time process, whilst avoiding the disadvantages in the manner described hereinbefore.

Figure 7:
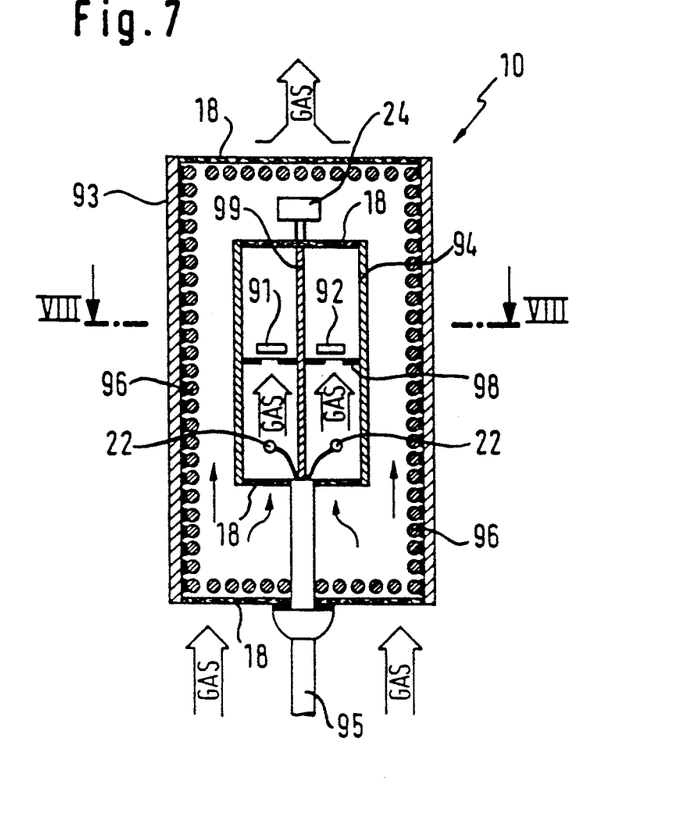
FIG. 7 An axial section through an example of a sensor system equipped with two spatially separated sensors.

FIG. 7 diagrammatically shows in axial section a first sensor system 10 with two sensors 91 and 92. The measurement casing 93 is cylindrical and contains in its interior a cylindrical inner casing 94. Both the measurement casing 93 and the inner casing 94 have in the lower region a circular inlet for the gas flow, which as a result of a forced flow passes upwards out of the smaller diameter inner casing 94 and the measurement casing 93. The inlet and outlet of the measurement casing 93 and inner casing 94 are in each case provided with filter surfaces 18.

For setting the temperature of the overall gas flow a heating means 96 with corresponding filament windings are provided on the inner face of the measurement casing 93 and are positioned axially and above the inlets.

The overall sensor system 10 is fixed by means of a stylized mounting support 95, which simultaneously serves as a cable guide to the sensors 91 and 92 or to the temperature sensors 22, or to the flow detector 24. The inner casing 94 is subdivided by a partition 99 into two semi-circular channels, in which the sensors 91 or 92 are placed on a support 98 in the gas flow.

This spatial separation of the sensors 91 and 92 consequently makes it possible to e.g. operate the sensor 91 with a voltage of approximately 1.1 V and the sensor 92 with a voltage of approximately 1.8 V. Thus, the sensor 91 is operated as a "dry" sensor, which measures the oxygen partial pressure without steam dissociation. By means of the sensor 92 determination takes place of the oxygen partial pressure, including the oxygen atoms resulting from steam dissociation.

The integration of this sensor system 10 into a measuring apparatus 30 takes place in accordance with the description relative to FIG. 3.

Figure 8:
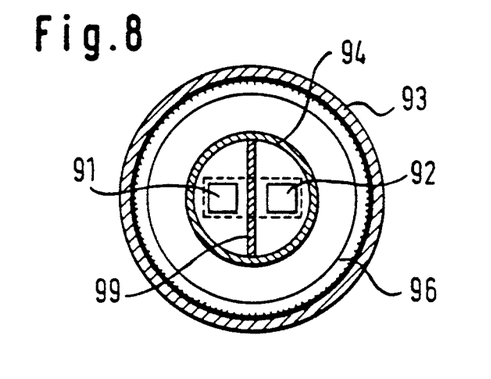
FIG. 8 A section along line VII—VII of FIG. 7.

In the cross-section according to FIG. 8 the sensor system 10 of FIG. 7 is shown along line VIII—VIII. The same reference numerals relate to the same components or means. FIG. VIII illustrates the coaxial arrangement of the measurement casing 93 and the radially smaller inner casing 94 with the spatial separation of the two sensors 91 and 92.

The construction of the sensor system 10 and the evaluation of the electrical signals of the sensors 91 and 92 consequently make it possible, by means of the current difference, which is proportional to the steam content of the gas to be measured, to precisely determine the moisture content. Taking account of the absolute pressure and the actual temperature of the gas to be measured, therefore it is possible to back-calculate all the other moisture measurement quantities by using corresponding computing electronics. Thus, with said long term-stable, zirconia-based current limiting sensors, the sensor system permits a rapid moisture measurement free from contamination effects.

Figure 9:
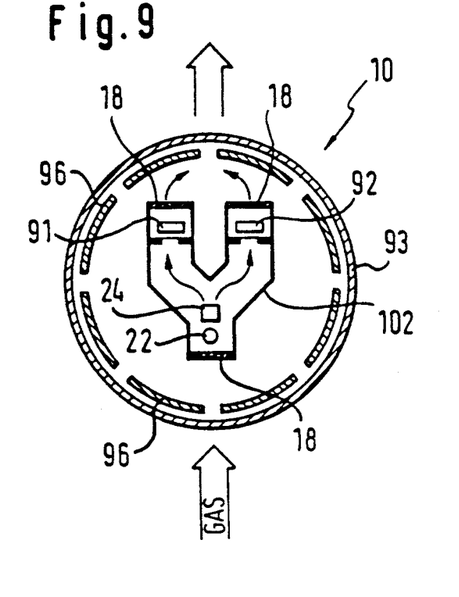
FIG. 9 Another example of a sensor system operating with two separate sensors.
Figure 10:
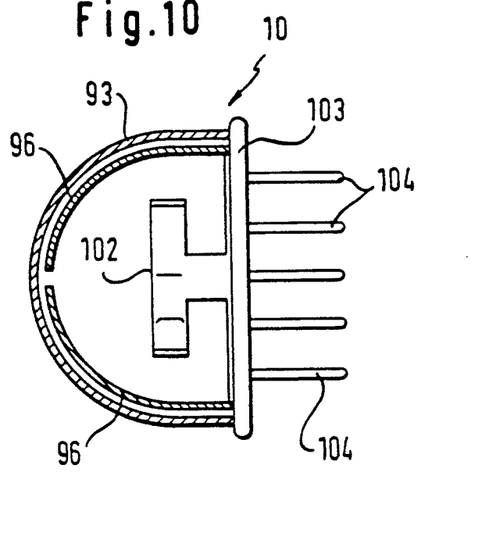
FIG. 10 A vertical section through the measurement casing of FIG. 9.

Another embodiment of a sensor system 10 is shown in cross-section in FIG. 9 and in axial section in FIG. 10. The measurement casing 93 is roughly hemispherical and in plan view surrounds the roughly Y-shaped inner casing 102. In FIG. 9 the measurement casing 93 is constructed as a filter, to whose inside are connected heating elements 96, between which there are radial flow openings for the inflowing gas.

The flow to the inner casing 102 takes place across a filter 18 and after traversing the temperature sensor 22 and the flow detector 24, the gas flow is split into two separate channels, in which are positioned the sensors 91 or 92. The outlets of the inner casing 102 are also provided with filters.

FIG. 10 makes it clear that the inner casing 102 is appropriately positioned in the central region of the measurement casing 93 and is spaced in table-like manner from the connection plate 103 up to which are led to the right the corresponding contact pins 104.

The function of the sensor system 10 is comparable with that described hereinbefore. The measurement gas flow is firstly regulated to the constant "balancing temperature". The two sensors 91 and 92 are operated in spatially separated manner in two different channels and with a different voltage, so that by means of the current characteristics shown in FIG. 6 the moisture content of the gas to be measured can be determined.

Figure 11:
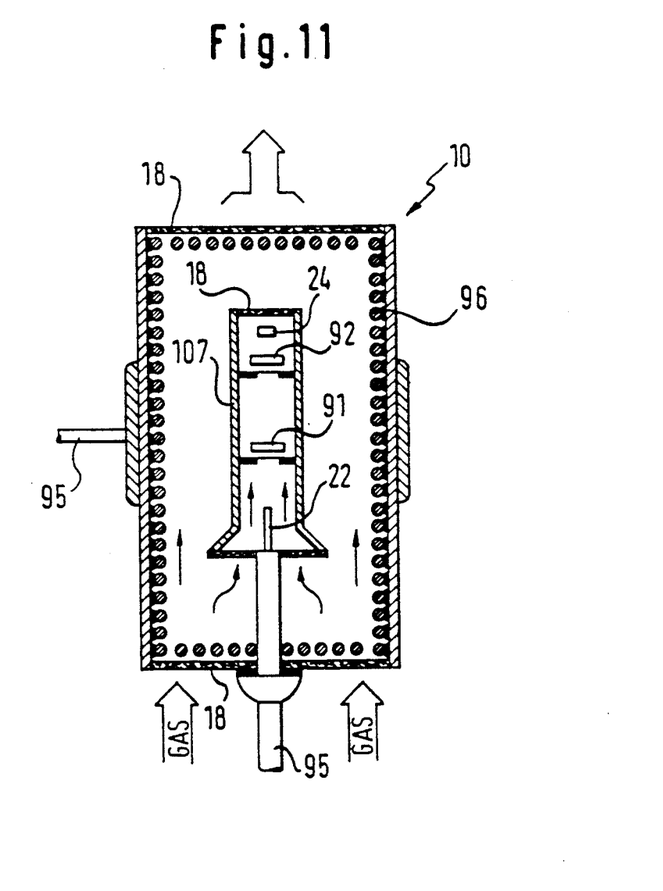
FIG. 11 Another embodiment of a sensor system operating with two separate sensors with series-connected sensors in the gas flow.

Another embodiment of the sensor system 10 is shown in axial section in FIG. 11. The same reference numerals correspond to the same components as in FIG. 7. The basic construction can be compared with the sensor system according to FIG. 7, but according to FIG. 11 the two sensors 91 and 92 are successively arranged in an inner casing 107. In this case the sensor 91 functions as a "dry" sensor, which only measures the oxygen content, i.e. it is operated with a voltage of approximately 1.1 V.

The following second sensor 92 in the gas flow functions as a "moist" sensor and is operated at a voltage of approximately 1.8 V. Thus, the steam contained in the gas to be measured is dissociated and consequently on sensor 92 measurement takes place of the oxygen contained in the gas and the dissociated oxygen atoms.

It is noteworthy that these dissociated oxygen atoms do not falsify the measurement result, because a sensor heating means is provided, which gives the convection a predetermined direction. By means of the corresponding current difference, it is possible to establish the moisture in a gas very accurately and in on-like manner in this simple example of the single-channel inner casing.

What we claim is:

1. A sensor system provided in a measurement casing for measurement of moisture in a gas, said system comprising two sensors, each sensor comprising an oxygen-ion-conducting zirconia plate with a flat electrode on either side and a diffusion casing connected in gas-tight relationship to the plate and having at least one gas diffusion opening, wherein said two sensors (91, 92) are spatially separated and of the same construction, wherein one sensor (92) is applied with a higher voltage bringing about the dissociation of the moisture content as steam, whilst the other sensor (91) is applied with a lower voltage, without dissociation of the moisture content, wherein the system further comprises a first heating device (74) to maintain the sensors (91, 92) at a fixed temperature, and a second heating device (96) including temperature measurement and regulating means for setting the gas at a specific temperature.

2. A sensor system according to claim 1, wherein the sensors (91, 92) are arranged in an inner casing (94) located in the measurement casing (93) and have a separate gas flows or are successively positioned in the gas flow.

3. A sensor system according to claim 2, wherein a device (52) is provided for producing a forced convection through the measurement casing (12, 93) and through the inner casing (94).

4. A sensor system according to claim 1, further comprising a microprocessor for at least the parallel processing of the output signals of the sensors (91, 92).

5. A sensor system according to claim 1, wherein a filter (18) of PTFE-sheeting is positioned upstream of the sensors (91, 92) and the temperature measuring and regulating means.

6. A sensor system according to claim 1, wherein the second heating device has heating elements close to the inner walls of the measurement casing (12, 93).

7. A sensor system according to claim 1, wherein a microprocessor is connected to a function generator (76) acting on the electrodes (64, 66) of the sensors (91, 92), wherein the current characteristics of the sensors are stored as a function of the oxygen and steam content and wherein it is possible to calculate from the difference of the current values of the two sensors (91, 92) the steam partial pressure and steam content of the gas to be measured.

8. A sensor system according to claim 1, wherein a gas flow supplied to the sensors has a connection to a dry gas supply (56).

9. A sensor system according to claim 1 wherein a temperature sensor (22) is positioned between the second heating device (96) and the sensors (91, 92) and a flow measuring device (24) is provided for the gas to be measured.

* * * * *